United States Patent [19]
Boehm

[11] Patent Number: 5,594,345
[45] Date of Patent: Jan. 14, 1997

[54] BATTERY CAPACITY INDICATOR FOR MOBILE MEDICAL EQUIPMENT

[75] Inventor: Manfred D. Boehm, Waukesha, Wis.

[73] Assignee: General Electric Company, Milwaukee, Wis.

[21] Appl. No.: 392,303

[22] Filed: Feb. 22, 1995

Related U.S. Application Data

[63] Continuation of Ser. No. 183,560, Jan. 19, 1994, abandoned.

[51] Int. Cl.⁶ .................................................. G01R 27/26
[52] U.S. Cl. ........................... 324/428; 324/427; 320/48
[58] Field of Search ............................. 324/427, 428, 324/429; 340/636; 320/48

[56] References Cited

U.S. PATENT DOCUMENTS

| | | | |
|---|---|---|---|
| 3,971,980 | 7/1976 | Jungfer et al. | 324/427 |
| 4,012,681 | 3/1977 | Finger et al. | 324/428 |
| 4,323,849 | 4/1982 | Smith | 324/428 |
| 4,558,281 | 12/1983 | Codd et al. | 324/427 |
| 4,679,000 | 7/1987 | Clark | 324/428 |
| 4,709,202 | 11/1987 | Roenck et al. | 340/636 |
| 4,816,768 | 3/1989 | Champlin | 324/428 |
| 4,949,046 | 8/1990 | Seyfang | 340/636 |
| 5,061,898 | 10/1991 | Oram et al. | 324/428 |
| 5,124,627 | 6/1992 | Okada | 340/636 |
| 5,266,880 | 11/1993 | Newland | 320/48 |
| 5,352,982 | 10/1994 | Nakazawa et al. | 320/48 |
| 5,357,203 | 10/1994 | Landau et al. | 320/48 |
| 5,381,350 | 1/1995 | Foring et al. | 324/427 |
| 5,426,589 | 6/1995 | Kitagawa et al. | 364/483 |
| 5,434,495 | 7/1995 | Toko | 324/427 |
| 5,479,085 | 12/1995 | Honda et al. | 360/48 |

FOREIGN PATENT DOCUMENTS

| 3213516 | 10/1983 | Germany | 324/428 |
|---|---|---|---|

*Primary Examiner*—Maura K. Regan
*Attorney, Agent, or Firm*—Quarles & Brady

[57] ABSTRACT

A mobile x-ray unit operates from a rechargeable battery in a number of different modes which draw current from the battery. Remaining battery capacity is calculated by integrating the current drawn from the battery in each of its operating modes, and periodically subtracting this value from a value indicative of remaining capacity. The result is displayed to provide an accurate indication of remaining battery capacity.

5 Claims, 4 Drawing Sheets

BATTERY CAPACITY INDICATOR FOR MOBILE MEDICAL EQUIPMENT

This is a continuation of application Ser. No. 08/183,560 filed Jan. 19, 1994, now abandonded.

BACKGROUND OF THE INVENTION

The field of the invention is battery powered medical equipment, and particularly, indicators of the remaining battery capacity on such equipment.

Mobile equipment is often battery powered so that it can be moved to any location and used without the need of an electrical power outlet. One such device, for example, is a mobile x-ray unit which is moved rapidly from patient-to-patient in the emergency department of a hospital. Such units must always have enough battery capacity available to produce a diagnostically useful x-ray, and if it is self-propelled, enough capacity to return the unit to its recharging station.

Battery powered medical equipment requires some means for indicating the remaining battery capacity. Typically, this takes the form of a voltmeter which indicates battery voltage. However, as shown in FIG. 1, because the battery voltage drops very little over much of the battery's usable capacity, and drops linearly over an even smaller portion of its usable capacity, this method of indicating battery capacity is not reliable. Normal voltage profile differences between battery manufacturers as well as changes in voltage profiles as the battery is cycled during normal use can result in misleading capacity indications. Such a variation is shown by the dashed line 2 in FIG. 1, where the battery voltage drops slightly at the outset and remains fairly constant until very little charge is remaining.

The difficulty of measuring battery capacity based on voltage is increased where accuracy is required while the battery still has substantial remaining charge. As shown in FIG. 1, when the battery is nearly discharged the voltage drops substantially and a warning indication based on low voltage may accurately indicate the remaining charge shown by cross hatching 3. On the other hand, where the warning indication must be made with a larger remaining charge as indicated by the cross hatching 4, the measurement of battery voltage may be a very inaccurate indication. For example, the measured voltage may properly indicate the remaining charge at dashed line 5 on a new battery, but the same voltage may trigger a much earlier indication at dashed line 6 after the battery is cycled a number of times.

SUMMARY OF THE INVENTION

The present invention relates to an improved battery capacity indicator, and particularly, to one which measures the actual battery usage and subtracts the used capacity from the known fully charged battery capacity to arrive at a remaining battery capacity that is indicated to the user. The battery usage may be measured directly by integrating battery current over time, or it may be measured indirectly by integrating over time the known current requirements of each mode of equipment operation.

A general object of the invention is to provide an accurate indication of remaining battery capacity. The capacity of the battery is known from the device's specification, for example, 20 ampere-hours. By measuring the current drawn from the battery during its use and integrating over time, a running total of the ampere-hours consumed is maintained and can be subtracted from the rated full capacity to indicate remaining battery capacity. This measurement is completely independent of battery voltage and is not, therefore, subject to the variation discussed above.

Another object of the invention is to provide an indication of remaining battery capacity without the need for any special sensors or measuring devices. The equipment drawing current from the battery has a finite number of operating modes, and each of these modes draws a known amount of battery current. The used battery capacity can therefore be measured indirectly by integrating over time the known current demand of each mode of operation as it is used. No separate current or voltage sensors are required.

DESCRIPTION OF THE PREFERRED EMBODIMENT

Figure 1:
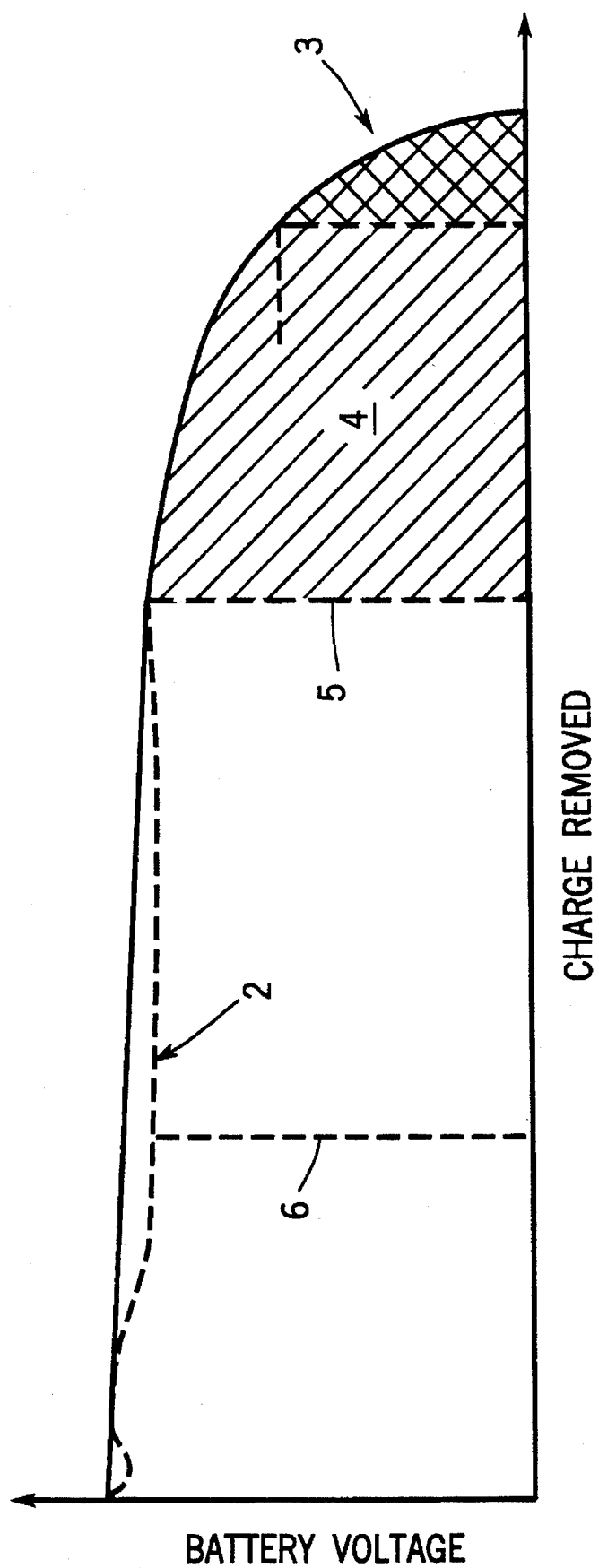
FIG. 1 is a graphic representation showing how battery voltage declines as a typical lead-acid battery is discharged.
Figure 2:
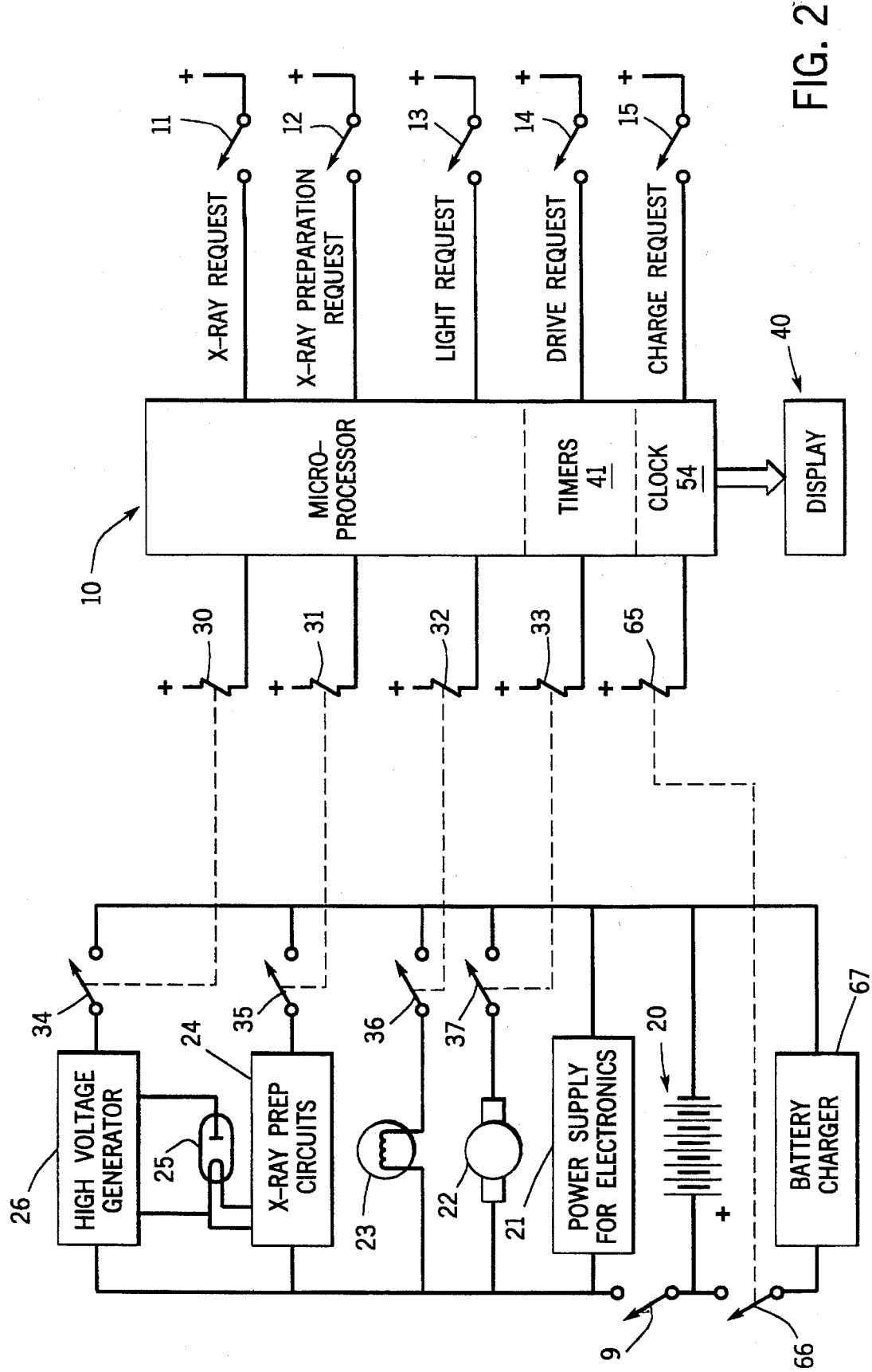
FIG. 2 is an electrical block diagram of a portable x-ray unit which incorporates a preferred embodiment of the invention.

Referring particularly to FIG. 2, a mobile x-ray unit is operated by a programmed microprocessor 10 which receives commands from a set of switches 11–15 that indicate its mode of operation. When a switch 9 is closed, the microprocessor 10 and other electrical components of the x-ray unit are powered by a rechargeable battery 20, which in the preferred embodiment is a lead-acid battery. The battery 20 drives a power supply 21 which provides electrical power of the desired voltage to the electronic circuits, including microprocessor 10, and it supplies much larger amounts of power to a number of other devices. These other devices include a drive motor 22 which propels the x-ray unit from one location to another, and a field light 23 which illuminates the area of the patient which will be x-rayed. When an x-ray is taken, the battery also supplies power to x-ray preparation circuits 24 that prepare an x-ray tube 25 for an exposure by heating its filament and rotating its anode. A high voltage generator 26 is enabled during the prescribed exposure time to provide the prescribed MA dose.

In response to commands input through the switches 11–14, the microprocessor 10 energizes relays 30–33 to operate corresponding contacts 34–37 in circuit with the operating elements 22–26. The microprocessor 10 thus controls which elements receive current from the battery 20 and for how long. As will be described below, this is used to measure the current discharged from the battery 20 and to provide an indication of the battery condition on a display 40.

There are five distinct loads on the battery 20 when the x-ray unit is turned on. These include: "idle" energy which is required by the electronics power supply 21; "drive" energy which is required by the motor 22 to propel the unit; "field light" energy which is required when the light 23 is turned on; "prep" energy which is required by circuit 24 to prepare the x-ray tube 25; and "x-ray" energy delivered by the tube 25 during the prescribed exposure. All of these loads except the drive motor 22 are relatively constant, known values. In the preferred embodiment, the drive motor current is assumed to be constant at a level required to propel the unit at top speed on a level surface. For these modes of operation, the energy discharged from the battery 20 is as follows:

$$\text{idle energy} = \text{elapsed idle time} \times 300 \text{ mA} \quad (1)$$

$$\text{drive energy} = \text{elapsed drive time} \times 3000 \text{ mA} \quad (2)$$

$$\text{field light energy} = \text{elapsed light time} \times 2500 \text{ mA} \quad (3)$$

$$\text{prep energy} = \text{elapsed prep time} \times 3000 \text{ mA} \quad (4)$$

The x-ray energy discharged is determined from the exposure prescription:

$$\text{x-ray energy} = \text{cumulative exposure energy} \times \text{conversion factor}, \quad (5)$$

where:

"conversion factor" is a measure of the x-ray generator efficiency and is 13 in the preferred embodiment.

Figure 3A:
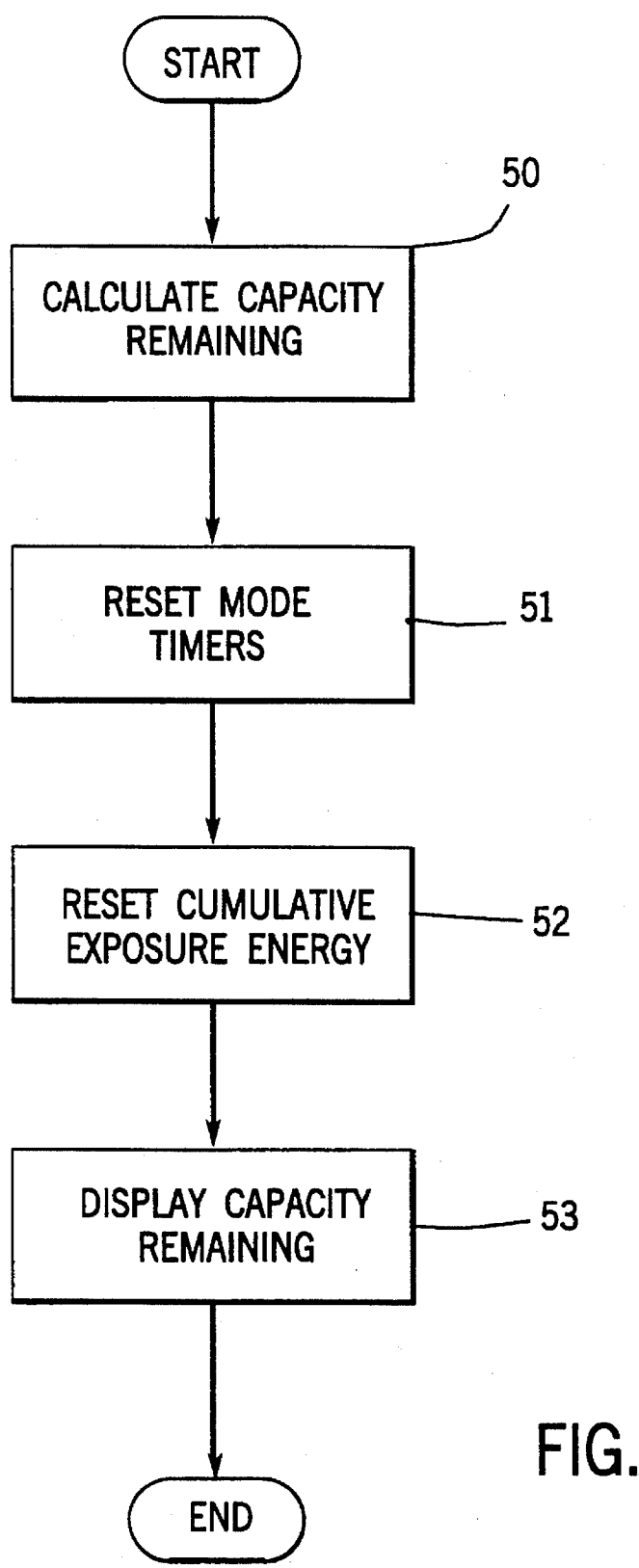
FIG. 3A and 3B are flow charts of programs executed by the unit of FIG. 2 to practice the present invention.

Referring particularly to FIG. 3A, approximately every 5 seconds the microprocessor 10 executes a program which updates the display 40 with a value indicating the remaining battery capacity. In the preferred embodiment this is a percentage of full battery capacity and it is calculated as indicated at process block 50 using the above equations (1) through (5) and the following:

$$\text{capacity} = \text{capacity} - \text{idle energy} - \text{drive energy} - \text{field light energy} - \text{prep energy} - \text{x-ray energy}.$$

This is converted to a percentage as follows:

$$\% = \text{capacity} / \text{fully charged capacity} \times 100.$$

Timers 41 are maintained for each mode of operation, and these are then reset to zero as indicated at process block 51 and the cumulative exposure energy is reset to zero at 52. The updated % value is then output to the display 40 at process block 53.

Figure 3B:
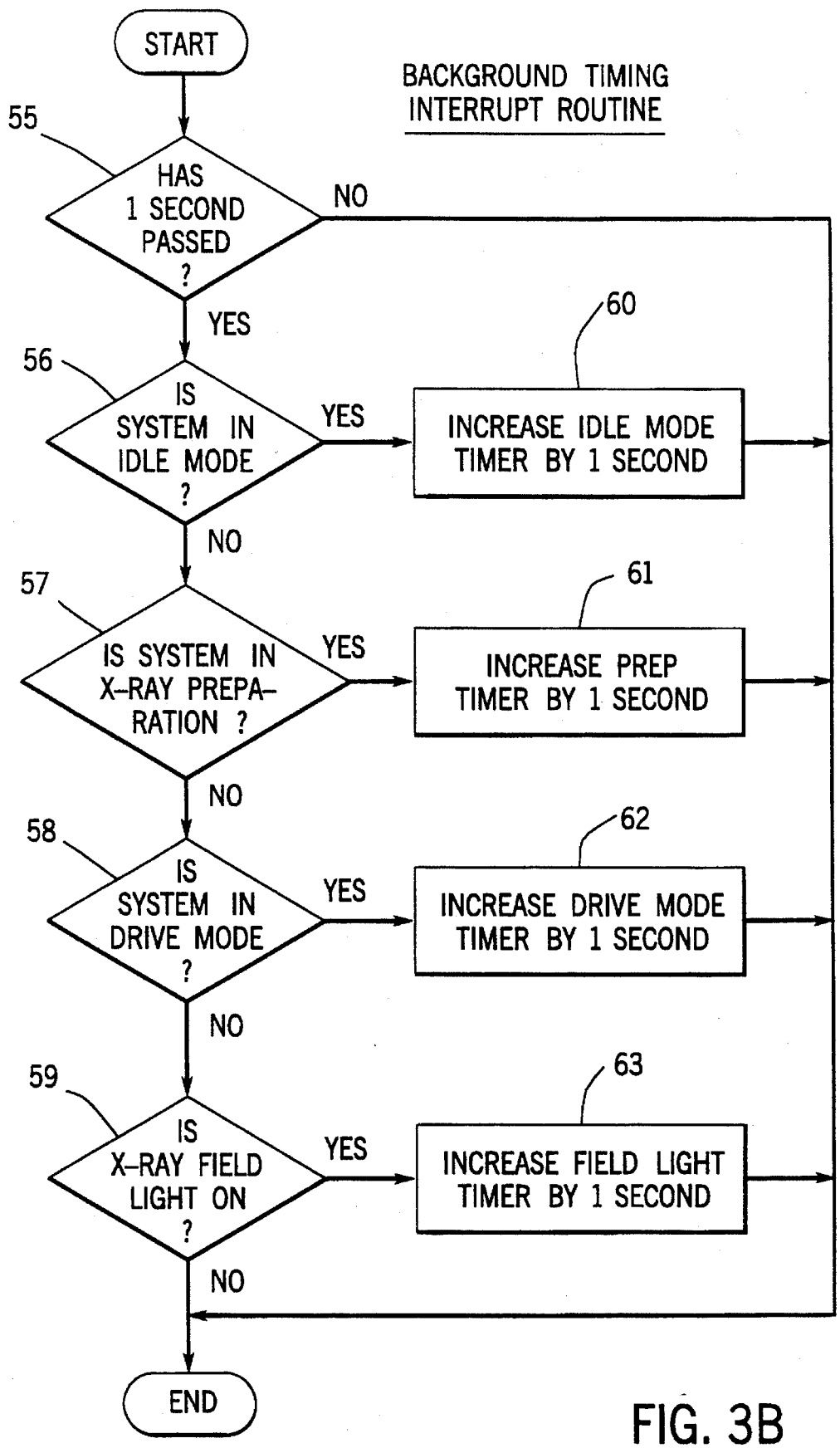

During the operation of the x-ray unit a program shown in FIG. 3B is executed periodically to update the mode timers 41. A clock 54 in the microprocessor 10 generates an interrupt every 25 milliseconds and the system is vectored to this program. As indicated at decision block 55, a test is made to determine if another second has elapsed, and if so the current mode(s) of operation is determined at decision blocks 56–59 and the appropriate mode timer(s) 41 is incremented one second at corresponding process block 60–63. The elapsed time in each mode of operation is thus accumulated for use by the above-described program to calculate the remaining battery capacity.

Two other programs are important to the implementation of the invention. The first is a program which controls the operation of the x-ray tube 25 during an exposure. In addition to its other functions, this program updates the "cumulative exposure energy" number used in equation (5) each time an exposure is performed. This is simply a multiplication of the prescribed mA dose times the prescribed exposure time, times the x-ray tube voltage. A second program is executed when the charge request switch 15 is closed. In addition to energizing a relay 65 to close a switch 66 and thereby connect a battery charger 67 to the battery 20, this program updates the value of "capacity" to reflect the increasing charge on the battery 20 as recharging progresses and to indicate the percentage of battery capacity available on display 40. At the completion of the recharging sequence, the battery is fully charged and the "capacity" value reflects this fact. When the display 40 is subsequently updated, it will indicate 100%.

It should be apparent to those skilled in the art that modifications can be made to the preferred embodiment described above without departing from the spirit of the invention. In addition, while the invention has particular application to a mobile x-ray unit, it can be applied to other battery operated equipment where an accurate indication of remaining battery capacity is required.

I claim:

1. In a system having a finite number of different operating modes that each draw a known amount of current from a battery, the combination comprising:

a set of timers, one for each of said different operating modes;

means for enabling the corresponding timer to accumulate time values while the system is operated in any of its operating modes;

means for periodically calculating the current drawn from the battery, including means for multiplying the accumulated time value in each timer by the known current draw for its corresponding operating mode;

means for calculating the remaining capacity of the battery including means for summing the values calculated by the last named means, and means for subtracting the resulting sum from a value indicating available battery capacity; and means for displaying the remaining capacity.

2. The system as recited in claim 1 in which the system is medical imaging equipment and the battery is rechargeable.

3. The system as recited in claim 2 in which the medical equipment is a mobile x-ray unit.

4. The system as recited in claim 3 in which one of the modes of operation energizes a drive motor that propels the mobile x-ray unit.

5. The system as recited in claim 1 in which the battery is rechargeable and the system includes means for recharging the battery and for increasing the value indicating available battery capacity by a corresponding amount.

\* \* \* \* \*